United States Patent [19]

Alexander et al.

[11] Patent Number: 4,965,072

[45] Date of Patent: Oct. 23, 1990

[54] GRANULATING COMPOSITION AND METHOD

[75] Inventors: Thomas A. Alexander, South Bend; Lawrence J. Daher, Elkhart, both of Ind.; Clarence L. Hancock, Edwardsburg, Mich.; Donald L. Peterson, Elkhart, Ind.

[73] Assignee: Miles Inc., Elkhart, Ind.

[21] Appl. No.: 266,649

[22] Filed: Nov. 3, 1988

[51] Int. Cl.$^5$ ............................ A61K 9/26; A61K 9/46
[52] U.S. Cl. ................................. 424/458; 424/461; 424/462; 424/439; 424/441; 424/465; 424/466; 424/493; 424/494; 424/495; 424/497; 424/498; 424/601; 424/606; 514/692; 514/715; 514/722
[58] Field of Search ............... 424/470, 461, 466, 462, 424/439, 441, 495, 493, 494, 497, 498, 601, 606; 514/692, 715, 722

[56] References Cited

U.S. PATENT DOCUMENTS

| | | | |
|---|---|---|---|
| 4,201,756 | 5/1980 | Saeman et al. | 424/490 |
| 4,439,453 | 3/1984 | Vogel | 424/470 |
| 4,582,709 | 4/1986 | Peters et al. | 424/601 |

Primary Examiner—Thurman K. Page
Attorney, Agent, or Firm—Mary G. Boguslaski

[57] ABSTRACT

The invention involves a granulating composition composed of an aqueous solution of magnesium sulfate heptahydrate and sodium hexametaphosphate. This composition can be used to prepare granules of ingredients for inclusion in any formulation for which rapid disintegration or dispersion are important factors. It is useful for tablets containing ingredients which are difficult to compress and is particularly useful for formulating swallowable tablets of a single non-soluble ingredient such as calcium carbonate. Disintegration times are markedly decreased.

7 Claims, No Drawings

GRANULATING COMPOSITION AND METHOD

FIELD OF THE INVENTION

The invention relates to a granulating composition and method of granulation which provides good granule formation, good tablet formula, compressibility and efficient disintegration of formulations in water. In particular, the invention can be used to decrease disintegration time of a swallowable tablet in the stomach or of an effervescent tablet in water.

BACKGROUND OF THE INVENTION

Tableting has always required balancing the need for a tablet which will withstand the stress of manufacturing, packaging and storage without breaking or fracturing with the need for a tablet which will to make the ingredient available for dissolution disintegrate and absorption. It is known that a hard compact tablet can be produced which will pass completely through the body.

The solution to this problem has been approached in many ways. One method is to use so called "super disintegrators" such as Ac-Di-Sol ®, available from FMC Corp., Philadelphia, Pa., a modified cellulose gum which promotes disintegration of a swallowable tablet in the stomach.

This invention provides another answer to the problem with a granulating composition which promotes active disintegration, can be used with normal tablet manufacturing procedures and provides a tablet with suitable handling characteristics. The composition can also be used advantageously with ingredients which are difficult to compress with normal tableting procedures.

SUMMARY OF THE INVENTION

The invention provides a granulating composition and a method of granulating.

The composition includes magnesium sulfate and sodium hexametaphosphate in aqueous solution. Magnesium sulfate heptahydrate is a readily available form of magnesium sulfate and ratios of sulfate to phosphate and total weight percentages given herein were calculated on the basis of the heptahydrate.

The composition can be used in a granulating procedure, comprising the steps of:

a. mixing a granulating composition, composed of an aqueous solution of magnesium sulfate heptahydrate and sodium hexametaphosphate in a ratio of about 10:1 to about 2:1 by weight with a total solid content of about 10 to 60% by weight, with an ingredient to be granulated to produce a uniformly wetted mixture;

b. drying the wetted mixture at a temperature between 40 and 100 degrees centigrade; and c. sizing the dried mixture to form a dried granulation mixture.

The granulated ingredient may then be used in any tablet formulation desired, effervescent or swallowable, or may be used in the granular form as desired.

DETAILED DESCRIPTION OF THE PREFERRED EMBODIMENTS OF THE INVENTION

The granulating composition as used herein is defined as an aqueous solution. The composition of the invention is composed of magnesium sulfate heptahydrate, sodium hexametaphosphate and water. The composition is primarily composed of the three ingredients with a total solid content of approximately 10 to 60% by weight. Other ingredients which are to be added to a final formulation in only a small amount may also be added to the composition.

This composition and method of granulating provide a tablet formulation which has both good compressibility and good disintegration characteristics. It is believed, but not relied upon, that the magnesium sulfate acts as a binder and that the sodium hexametaphosphate acts both to augment the binding property of the composition and to improve the disintegration time. The ratio of sulfate to hexametaphosphate can be varied between about 10 to 1 to about 2 to 1 by weight depending on the desired characteristics of the final formulation. A preferred ratio is about 4 to 1 by weight for ingredients with particular compression problems such as calcium carbonate, magnesium hydroxide or acetaminophen. The total solid content of the composition can vary from about 10 to 60% by weight. A preferred solid content of the composition for granulating calcium carbonate or magnesium hydroxide is about 40 to 50% by weight.

All ratios and weight percentages given are calculated on the basis of magnesium sulfate heptahydrate. However, it is to be understood that while this is a readily available commercial form of magnesium sulfate, anhydrous magnesium sulfate could be used making the easily calculated allowance for the difference in molecular weight to calculate the ratios to be used. Therefore, as used herein, magnesium sulfate heptahydrate is equivalent to magnesium sulfate or any of the various hydrated forms.

The composition and method are particularly advantageously used in a single non-soluble ingredient formulation such as a calcium carbonate tablet. This granulating composition provides a calcium carbonate tablet with a decreased disintegration time and provides an improved formulation for BIOCAL ®, available from MILES INC, Elkhart, Ind. However, the composition can also be used to formulate other difficult to granulate ingredients such as magnesium hydroxide for addition to vitamin formulations such as STRESSGARD ®, also available from MILES INC, or for effervescent ingredients such as sodium bicarbonate and citric acid useful in effervescent formulations.

The composition and method are not limited in use to tableting but may be used in powdered drink formulations where increased dispersibility will provide added ease of use.

The method of granulating particularly preferred ingredients includes the steps of a mixing an ingredient chosen from calcium carbonate, magnesium hydroxide, acetaminophen, sodium bicarbonate or citric acid with an aqueous granulating composition composed of magnesium sulfate heptahydrate and sodium hexametaphosphate in a ratio of about 4 to 1 by weight with a solid content of 40 to 50% by weight until a uniformly wetted mixture is produced;

b. drying the wetted mixture at a temperature between 40 and 100 degrees centigrade; and c. sizing the dried mixture to produce a free flowing dried granulation.

Mixing may be accomplished in any suitable mixer. For commercial manufacture a high intensity mixer such as a Littleford Lodige mixer/granulator is preferred. Other equipment such as a fluid bed granulator or a spray drier may also be used. In the latter cases drying of the mixture is accomplished with the same equipment as mixing and the sizing step may not be required.

The mixture is then dried to drive off water used as a solvent; and when desired, some or all of the water of hydration of the magnesium sulfate. In order to remove the about four moles of water of hydration, the temperature should be in excess of 70° C. but below 100° C. Other temperatures and periods of drying may be used as long as the degree of drying is suited to the needs of the end product. Drying is commonly accomplished in a kiln on trays at approximately 90 degrees centigrade for a period of not less than 12 hours. The mixture may also be dried in a fluid bed drier.

The dried mixture is then sized by passing it through a suitable milling machine to produce a free flowing granulation. It has been found that the finished dried granulation mixture is composed of particles of the granulated ingredient coated with the sulfate/phosphate composition.

The finished dried granulation may be used as an ingredient in desired tablet formulations and may be used to produce tablets by normal manufacturing methods. The dried granulation may also be used directly if a powder is preferred.

The following examples describe granulation formulations which were prepared. While the examples serve to illustrate the invention, they are not to be interpreted as limiting its scope, which is defined solely by the claims. One skilled in the art will be able to make such variations, substitutions and changes in the components of the granulating compositions, ingredients to be granulated and of the conditions of granulation as may seem desirable.

EXAMPLES

Calcium Carbonate Granulation

Calcium carbonate is granulated with the granulating composition of the invention as follows:

1.44 kilograms of sodium hexametaphosphate (Vitrafos ®, Stauffer Chemical Co., Westport, Conn.) is dissolved in 7.2 kilograms of water with mixing. 5.76 kilograms of magnesium sulfate heptahydrate (Epsom Salt USP, Dow Chemical USA, Midland, Mich.) are added to the previous solution and dissolved to produce a granulating composition containing a 4:1 ratio of the sulfate to phosphate with a total solid content of approximately 50% (as calculated including the waters of hydration).

14.4 kilograms of the granulating composition is placed in a solution transfer tank. A Lodige Mixer Model FM-130-D, Littleford Bros., Inc., Cincinnati, Ohio, is charged with 68.18 kilograms of calcium carbonate (Whiton F ®, HM Royal, Inc., Trenton, N.J.). The solution is transferred from the tank to the mixer while the mixer is running. The mixer is run for approximately twelve minutes or until densification of the powder is apparent and the wetted mixture is discharged into collection drums. The wet granulation is spread on kiln trays. The trays are placed in a kiln and dried at 90° C. for twelve hours.

The dried granulation is removed from the kiln and assayed for moisture content. The dried mixture is passed through a Fitzpatrick Comminutor (Model D), WJ Fitzpatrick Co., Chicago, Ill. equipped with a swinging blade milling head, knives forward. For a calcium carbonate tablet the milling head of the Fitzpatrick is set at about 2500 rpm with a 2A screen. The coating in the final granulation is about 5 to 10% of the total solid content by weight.

The granulated material is then used in normal tableting procedures to produce a swallowable tablet.

Magnesium Hydroxide Granulation

Magnesium hydroxide is granulated as above with the exception that 68.0 kilograms of magnesium hydroxide is mixed with the granulating composition. Again, the coating comprises about 5 to 10% of the total solids by weight in the final dried granulation. The granules of magnesium hydroxide produced using the composition of this invention have been used with other ingredients to prepare a vitamin/mineral tablet.

Obviously, many modifications and variations of the invention as set forth may be made without departing from the spirit or scope of the invention.

What is claimed is:

1. A granulating composition comprising magnesium sulfate and sodium hexametaphosphate in an aqueous solution.

2. The granulating composition of claim 1 wherein the magnesium sulfate heptahydrate and sodium hexametaphosphate are present in a ratio by weight of about 10 to 1 to about 2 to 1, with a total solid content of about 10 to 60% by weight.

3. The granulating composition of claim 2 wherein the ratio by weight is about 4 to 1, with a total solid content of about 40 to 50% by weight.

4. A method of preparing a dried granulated mixture, comprising the steps of:
   a. mixing an ingredient chosen from calcium carbonate, magnesium hydroxide, acetaminophen, sodium bicarbonate or citric acid with a granulating composition composed an aqueous solution of magnesium sulfate heptahydrate and sodium hexametaphosphate in a ratio of about 4 to 1 by weight with a solid content of 40 to 50% by weight until a uniformly wetted mixture is produced;
   b. drying the wetted mixture between about 40 and 100 degrees centigrade; and
   c. sizing the dried mixture to produce a free flowing granulation.

5. A rapidly disintegrating tablet for the delivery of an effective amount of calcium carbonate, comprising:
   calcium carbonate granules coated with magnesium sulfate hydrate and sodium hexametaphosphate in a ratio of about 4 to 1 by weight wherein the coating comprises about 5 to 10% of the total solids by weight.

6. A granulation of magnesium hydroxide, comprising:
   magnesium hydroxide granules coated with magnesium sulfate hydrate and sodium hexametaphosphate in a ratio of about 4 to 1 by weight wherein the coating comprises about 5 to 10% of the total solids by weight.

7. A vitamin tablet including at least an effective amount of magnesium hydroxide incorporated as the granulation of claim 6.

* * * * *